(12) United States Patent
Popovsky (10) Patent No.: US 7,201,742 B2
(45) Date of Patent: Apr. 10, 2007

(54) SHEATH FOR A NEEDLE ASSEMBLY (75) Inventor: Frank Popovsky, Tahmoor (AU)

(73) Assignee: bioMD Limited, Perth (AU)

( * ) Notice: Subject to any disclaimer, the term of this patent is extended or adjusted under 35 U.S.C. 154(b) by 200 days.

(21) Appl. No.: 10/495,404

(22) PCT Filed: May 22, 2003

(86) PCT No.: PCT/AU03/00617

§ 371 (c)(1),
(2), (4) Date: May 5, 2004

(87) PCT Pub. No.: WO2004/018024

PCT Pub. Date: Mar. 4, 2004

(65) Prior Publication Data

US 2004/0267210 A1    Dec. 30, 2004

(30) Foreign Application Priority Data

Aug. 26, 2002   (AU) .............................. 2002950988

(51) Int. Cl.
*A61M 5/00* (2006.01)

(52) U.S. Cl. ........................ 604/263; 604/110

(58) Field of Classification Search ................ 604/110, 604/240, 192, 198, 263, 164.08
See application file for complete search history.

(56) References Cited

U.S. PATENT DOCUMENTS

| | | | | |
|---|---|---|---|---|
| 4,664,654 A | * | 5/1987 | Strauss | 604/198 |
| 4,702,738 A | | 10/1987 | Spencer | |
| 5,017,189 A | * | 5/1991 | Boumendil | 604/192 |
| 5,195,983 A | * | 3/1993 | Boese | 604/192 |
| 5,403,286 A | | 4/1995 | Lockwood | |
| 5,984,899 A | | 11/1999 | D'Alessio et al. | |
| 6,221,058 B1 | * | 4/2001 | Kao et al. | 604/263 |

FOREIGN PATENT DOCUMENTS

| | | |
|---|---|---|
| DE | 19543313 A1 | 6/1997 |
| WO | WO 91/11212 A1 | 8/1991 |
| WO | WO 0191837 A1 | 12/2001 |

* cited by examiner

*Primary Examiner*—Sharon E. Kennedy
(74) *Attorney, Agent, or Firm*—Townsend and Townsend and Crew LLP (57) ABSTRACT

A needle assembly includes an elongate needle mount (10), a needle (12), and a sheath (14) mounted on the elongate needle mount (10) for reciprocal axial movement between a forward position whereat the sheath (14) covers the needle (12) and a rearward position whereat the needle (12) is exposed.

12 Claims, 7 Drawing Sheets

SHEATH FOR A NEEDLE ASSEMBLY

CROSS-REFERENCES TO RELATED APPLICATIONS

This application claims the priority of Australian Patent Application 2002950988 filed Aug. 26, 2002, and is a U.S. National Phase application of PCT/AU03/00617 filed May 22, 2003, both of which disclosures are incorporated herein by reference.

TECHNICAL FIELD

This invention relates to a needle assembly.

BACKGROUND OF INVENTION

It is very well recognized that it is desirable to protect a needle before and after use in order to prevent needle-stick injuries, and also to ensure that the needle cannot be deliberately or accidentally re-used. To this end, the prior art is crowded with a multitude of syringes having sheaths which can be locked in a post-use position whereat the needle is covered by the sheath.

SUMMARY OF INVENTION

The present invention provides a needle assembly as defined in the following claims. Preferred features of the needle assembly will be apparent from the following description.

DESCRIPTION OF DRAWINGS

In order that this invention may be more easily understood and put into practical effect, reference will now be made to the accompanying drawings which illustrate a preferred embodiment of the invention, wherein.

DESCRIPTION OF PREFERRED EMBODIMENT OF INVENTION

Figure 1:
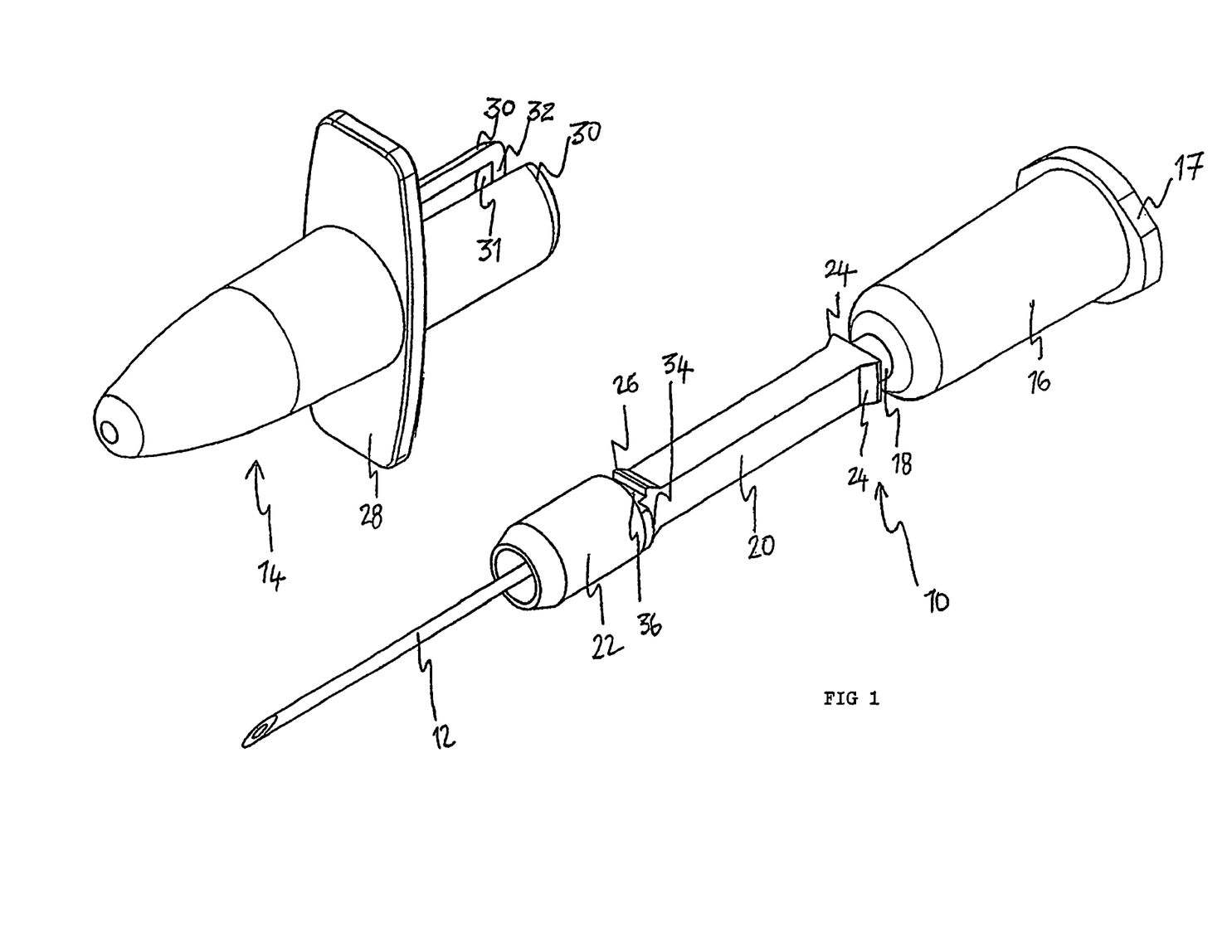
FIG. 1 is an exploded perspective view of a needle assembly according to the present invention.

With reference firstly to FIG. 1, there is illustrated an exploded perspective view of a needle assembly according to the present invention. The needle assembly includes an elongate needle mount 10, a needle 12 extending forwardly from the needle mount 10, and a sheath 14 which in use is mounted on the needle mount 10. It will be understood from the following description that the needle mount 10 is sufficiently elongate to accommodate reciprocation of the sheath 14 on the needle mount 10.

Typically, the components of the needle assembly, with the exception of needle 12, will be manufactured from plastics material.

The needle mount 10 has a rearward frusto-conical axial portion 16 which terminates in a flange 17. The rearward frusto-conical axial portion 16 is adapted to receive the forward end of a syringe (not illustrated).

Immediately forward of the frusto-conical axial portion 16 is a circular-cross-section axial portion 18. Forward of the circular-cross-section axial portion 18 is a square-cross-section axial portion 20. Forward of square-cross-section axial portion 20 is a generally cylindrical axial portion 22 with the needle 12 extending from the forward end thereof.

The square-cross-section axial portion 20 defines four sides comprising a pair of lateral sides, and upper and lower sides as shown in FIG. 1. The rearward ends of the lateral sides of square-cross-section axial portion 20 terminate in laterally extending first ramps 24. The forward ends of the upper and lower sides of the square-cross-section axial portion 20 terminate in upwardly and downwardly extending second ramps 26.

Still referring to FIG. 1, the sheath 14 includes opposed tabs 28 for engagement by the fingers of the person using the needle assembly, and the rearward end of the sheath 14 terminates in a bifurcated arrangement which defines a pair of laterally flexible resilient members 30. Each resilient member 30 includes a forwardly-directed internal surface 31, an inwardly-directed surface 32 which in use engages the sides of square-cross-section axial portion 20, and a rearwardly-directed surface 33 (best seen in FIG. 6).

Figure 2:
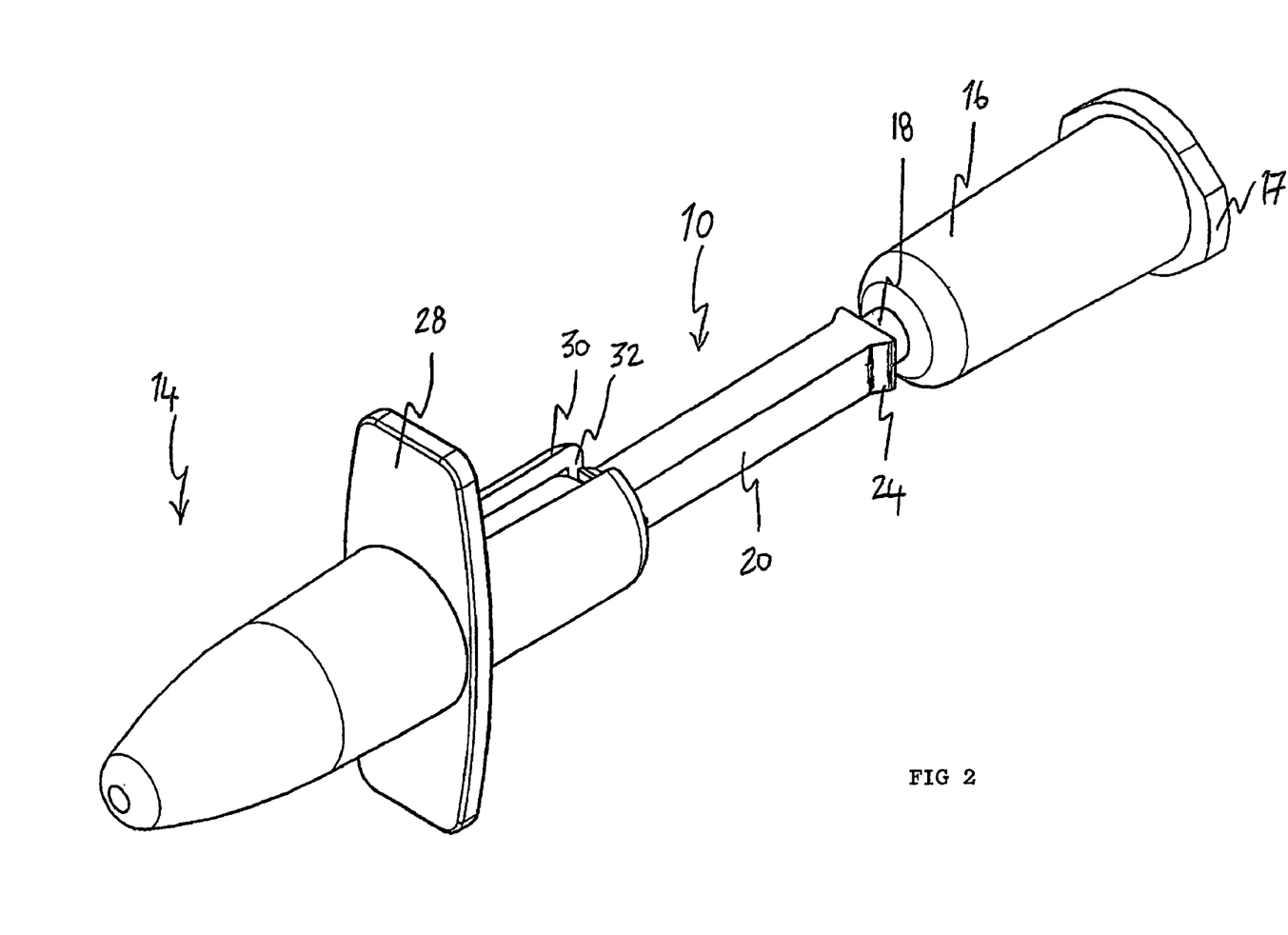
FIG. 2 is a perspective view of the needle assembly with the sheath in the pre-use, needle-protected position.

Turning now to FIG. 2, the assembled needle assembly is shown in the pre-use, needle-protected position. In this position, the sheath 14 is biased in a forward direction relative to the needle mount 10 by virtue of an internal compression spring 38 (refer to FIGS. 6 and 7). The sheath 14 is prevented from disengaging from the needle mount 10 in the forward direction by virtue of the engagement of the forwardly-directed internal surface 31 of the sheath 14 with a laterally-extending and rearwardly-facing surface 34 of the needle mount 10.

Figure 3:
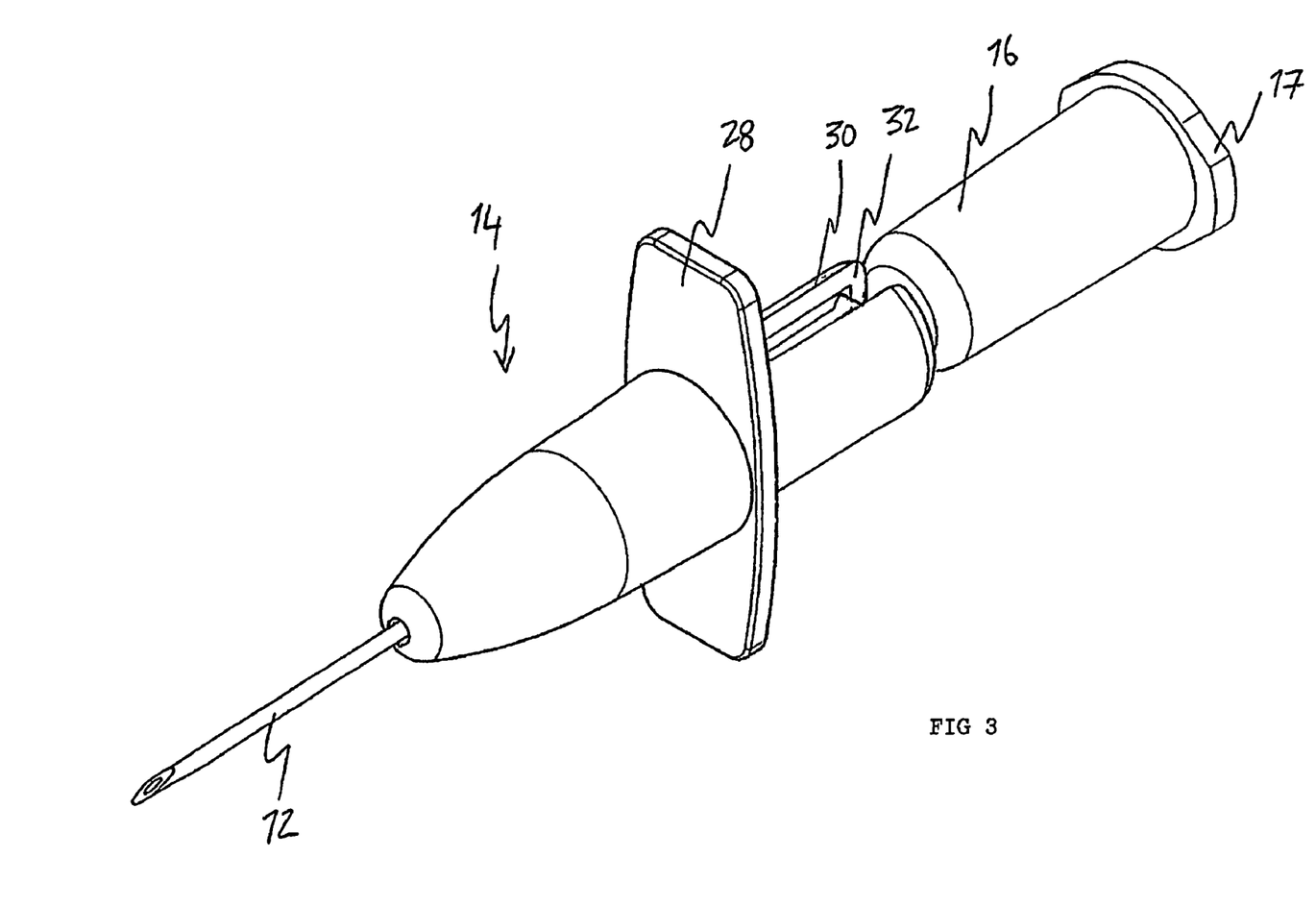
FIG. 3 is a perspective view of the needle assembly with the sheath in the ready-for-use, needle-exposed position.

Turning now to FIG. 3, the sheath 14 has been pulled rearwardly relative to the needle mount 10 to a position whereat the needle 12 is exposed and ready for use. During the rearward travel of the sheath 14 relative to the needle mount 10, the compression spring 38 has been compressed and the inwardly-directed surfaces 32 have slid along the respective lateral sides of the square-cross-section axial portion 20 and have been urged apart by the laterally-extending first ramps 24. Once the resilient members 30 have passed over the laterally-extending first ramps 24, they snap inwardly to a position whereat the inwardly-directed surfaces 32 engage the circular-cross-section axial portion 18. Concurrently, the internal forwardly-directed surfaces 31 of sheath 14 engage the rearward surfaces of the laterally-extending first ramps 24 such that the sheath 14 cannot move in the forward direction relative to the needle mount 10 under the effect of the compression spring 38.

Figure 4:
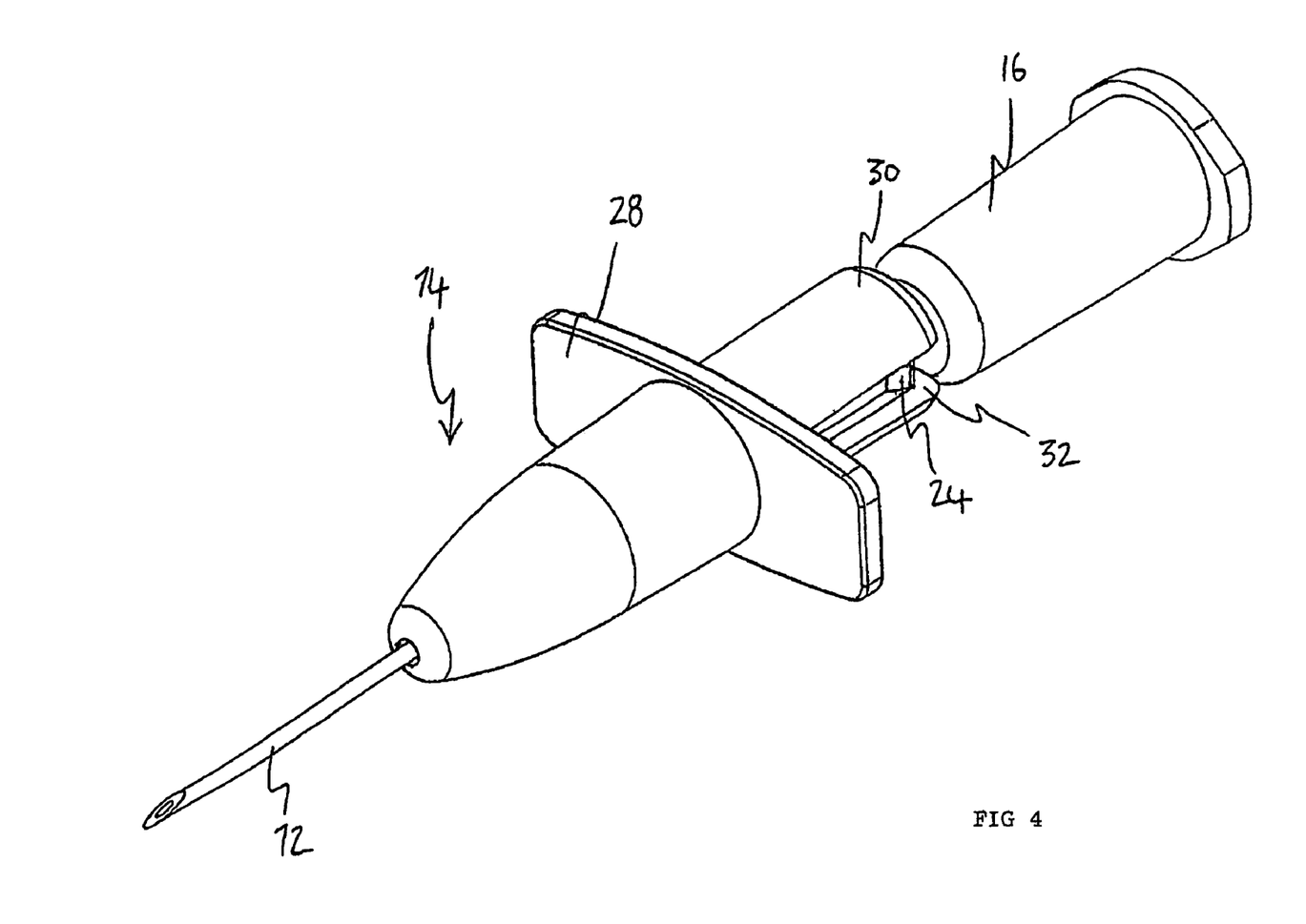
FIG. 4 is a perspective view of the needle assembly in the post-use, needle-exposed position.

Subsequent to the injection(s) occurring, the sheath 14 is axially rotated through 90° relative to the needle mount 10 to the position shown in FIG. 4. The shield 14 can be rotated in either direction relative to the needle mount 10 in the illustrated embodiment. In other embodiments the circular-cross-section axial portion may be only partially circular in cross-section (e.g. two opposed quadrants are circular) such that the shield 14 can only rotate in one direction relative to the needle mount 10.

Figure 5:
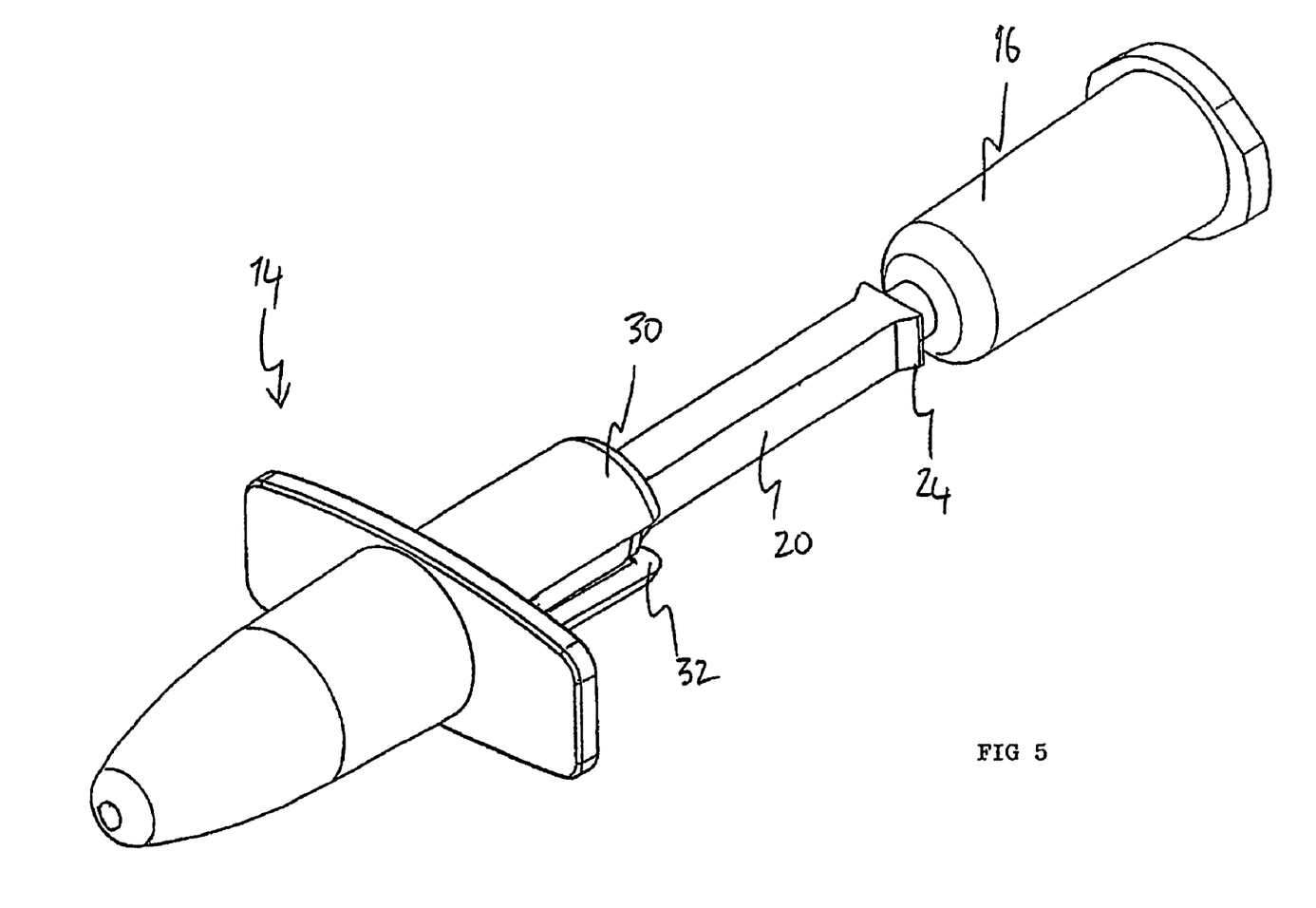
FIG. 5 is a perspective view of the needle assembly in the post-use, needle-protected position.

Rotation of the sheath 14 relative to the needle mount 10 is possible by virtue of the fact that inwardly-directed surfaces 32 of the needle mount 14 engage the circular-cross-section axial portion 18 of the needle mount 10. When the sheath 14 reaches the rotative position shown in FIG. 4, it is then free to move in the forward direction under the influence of the compression spring 38 to the position shown in FIG. 5 due to the fact that the resilient members 30 have disengaged from the laterally-extending first ramps 24.

During forward travel of the sheath 14 relative to the needle mount 10, the compression spring 38 expands and the inwardly-directed surfaces 32 of the needle mount 14 slide along the upper and lower sides of the square-cross-section axial portion 20 of the needle mount 10. As the sheath 14 reaches the forward position illustrated in FIG. 5, the resilient members 30 are spread apart as they pass over the upwardly- and downwardly-directed second ramps 26.

After passing over the second ramps 26, the resilient members 30 snap inwardly such that inwardly-directed surfaces 32 engage outwardly-directed planar surfaces 36 (refer to FIG. 1) provided on the needle mount 10. Subsequent rearward movement of the sheath 14 relative to the needle mount 10 is prevented by virtue of engagement of the rearward surfaces 33 of the sheath 14 with the forwardly-directed surfaces of the second ramps 26. Further, the sheath 14 cannot rotate relative to needle mount 10 by virtue of the engagement of inwardly-directed surfaces 32 with the outwardly-directed planar surfaces 36 of the needle mount 10. In this regard, it will be appreciated that while the resilient members are sufficiently resilient to pass over first ramps 24 and second ramps 26, they are not so resilient as to easily allow rotation of the shield 14 when it is in the position illustrated in FIG. 5 whereat the resilient members are engaged with the outwardly-directed planar surfaces 36 of the needle mount. Rather, substantial force would have to be applied to rotate the shield when it is in the locked position shown in FIG. 5.

It will also be understood that, because of the resilience of the resilient members 30, the square-cross-section axial portion 20 of the needle mount need not be perfectly square, but may actually be rectangular in cross-section. In this regard, it may be desirable to make the "square" section taller than it is wide so that the degree of pre-load on the resilient members is greater after the shield 14 has been rotated to the orientation shown in FIGS. 4 and 5. Similarly, the resilient members 30 can accommodate imperfections in the "roundness" of the circular-cross-section axial portion 18.

Figure 6:
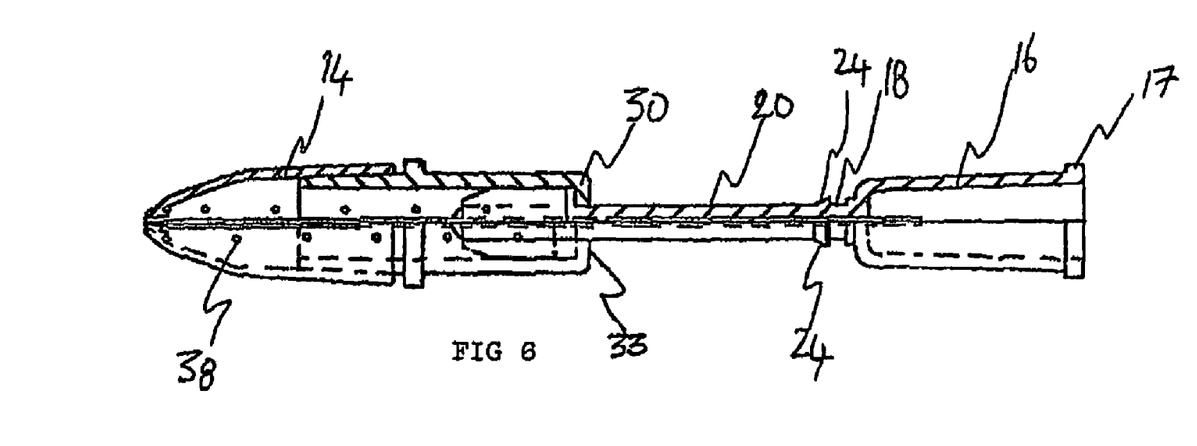
FIG. 6 is a partially-sectioned plan view of the needle assembly of FIG. 2.
Figure 7:
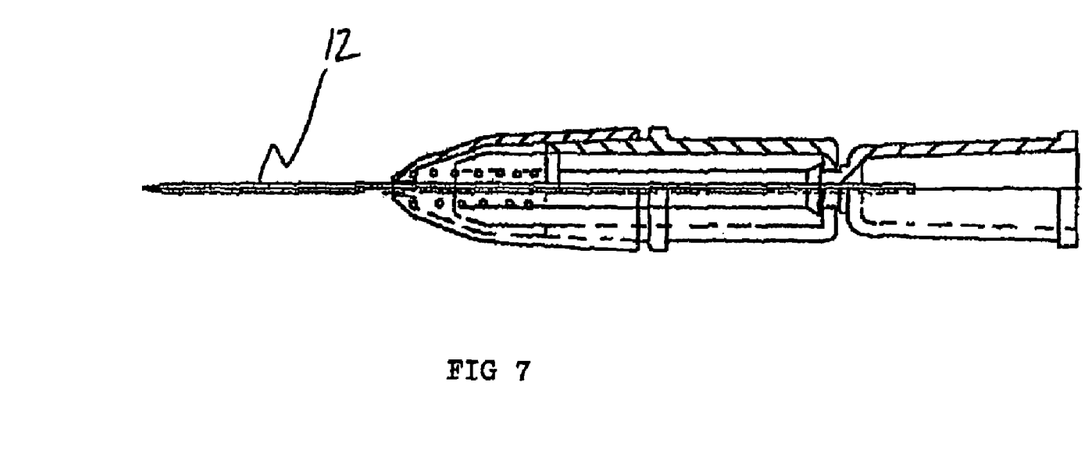
FIG. 7 is a partially-sectioned plan view of the needle assembly of FIG. 3.

FIGS. 6 and 7 are partially sectioned plan views corresponding to FIGS. 2 and 3, respectively. FIGS. 6 and 7 illustrate some hidden details which may not be readily apparent from the perspective views shown in FIGS. 1 to 5, particularly compression spring 38 which is provided between the forward end 22 of the needle mount 10 and the interior forward end of sheath 14.

Figure 8:
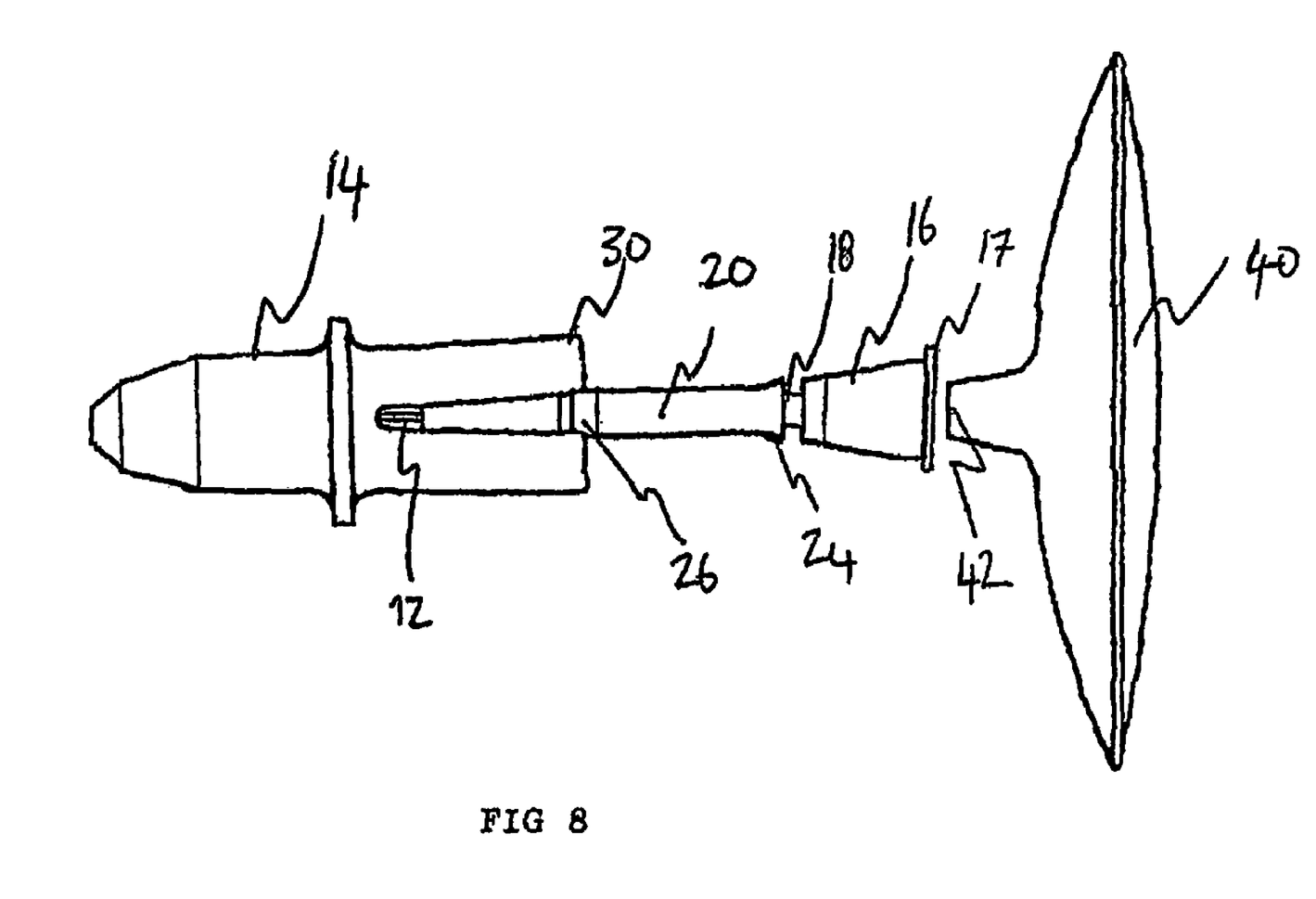
FIG. 8 is a plan view of the needle assembly of claim 2 shown ready for docking.

Typically, the needle assembly 10 will be mounted on a conventional syringe comprised of a fluid-containing barrel and rearwardly-extending plunger assembly. The syringe may be either pre-filled or not. The present invention is also suitable for use with less conventional low-volume "syringes" such as is illustrated in FIG. 8. In the case of FIG. 8, the traditional barrel and plunger assembly has been replaced with a flexible fluid-containing bellows 40. In this particular embodiment, the fluid-containing bellows 40 is urged into engagement with the frusto-conical portion 16 of the needle mount. During engagement, a rearwardly-extending section of needle 12 (refer to FIG. 7) pierces a frangible membrane 42 on the forward end of the fluid-containing bellows 40 such that the interior of the fluid-containing bellows 40 is in fluid communication with the interior of needle 12.

An ancillary benefit of the elongate needle mount 10 of the present invention is the fact that there is a relatively large axial length of the needle 12 passing through the body of the needle mount 10. This facilitates bonding of the needle 12 to the needle mount 10, which assures a secure fixture which is both reliable in use and cost-effective in manufacture.

In one possible embodiment the forward end of shield 14 through which the needle 12 passes may be sealed with a frangible membrane so that the shield 14 cannot easily move against the spring bias from the position shown in FIG. 2 to the position shown in FIG. 3. Rather, the needle would have to puncture the frangible membrane at the forward end of the shield 14 during movement of the shield from the position shown in FIG. 2 to the position shown in FIG. 3.

Another significant advantage of the present invention is the fact that it is suitable for use with the conventional hypodermic syringe, and "syringes" such as the type illustrated in FIG. 8. In this regard, prior art designs have mounted the sheath for reciprocating movement on the barrel of the syringe. This has dictated that the barrel of the syringe be customized to receive the sheath. In the present case, the sheath 14 is mounted for reciprocal movement on the needle mount 10 and accordingly a conventional cylindrical barrel can be used.

In the preferred embodiment the resilience is designed into the shield 14 by virtue of the materials chosen, the thickness of the material, and the bifurcated design of the shield. However, it is also possible for the shield to be rigid and for the resilience to be designed into the ramps on the needle mount 10; e.g. the ramps could be resilient flaps which deform inwardly as the shield passes over them.

In the preferred embodiment there are pairs of resilient members and pairs of sides of the needle mount engaged by the resilient members. However, in other embodiments, there may be more or less resilient members and a corresponding numbers of sides of the needle mount engaged by the resilient member(s).

It will of course be realized that while the above has been given by way of an illustrative example of this invention, all such and other modifications and variations hereto, as would be apparent to persons skilled in the art, are deemed to fall within the broad scope and ambit of this invention as is herein set forth.

The invention claimed is:

1. A needle assembly adapted to be used with a conventional syringe and including:
   an elongate needle mount having a forward end and a rearward end spaced along an axis, wherein the rearward end of the needle mount is adapted to be mounted directly onto a forward end of a conventional syringe;
   a needle extending axially from the forward end of the elongate needle mount; and
   a sheath mounted on the elongate needle mount for reciprocal axial movement between a forward position whereat the sheath covers the needle and a rearward position whereat the needle is exposed, wherein the sheath is initially in the forward position and is adapted to be moved without rotation to the rearward position whereat it is retained, and wherein rotation of the sheath relative to the elongate needle mount about the axis releases the sheath to return to a final forward position, and wherein the needle mount and the sheath co-operate to define a first path along which the sheath moves from the initial forward position to the rearward position, and wherein the needle mount and the sheath co-operate to define a second path along which the sheath moves from the rearward position to the final forward position, said second path being angularly spaced about said axis relative to said first path.

2. A needle assembly adapted to be used with a conventional syringe and including:
   an elongate needle mount having a forward end and a rearward end spaced along an axis, wherein the rearward end of the needle mount is adapted to be directly mounted onto a forward end of a conventional syringe;
   a needle extending axially from the forward end of the elongate needle mount; and
   a sheath mounted on the elongate needle mount for reciprocal axial movement between a forward position whereat the sheath covers the needle and a rearward position whereat the needle is exposed, characterized in that prior to use the sheath is in a forward position, and the sheath can be moved to a rearward position whereat it is retained during use, and wherein after use the sheath can be released to return to a final forward position whereat it is locked to prevent needle sticks, wherein the needle mount includes a retaining mechanism co-operating with the sheath to retain the sheath in a rearward position during use, wherein the needle mount includes a locking mechanism co-operating with the sheath to lock the sheath in the final forward position after use, and wherein the retaining mechanism and the locking mechanism are angularly spaced about said axis, such that after use the sheath must be rotated about the axis in order to disengage the sheath from the retaining mechanism and subsequently engage the sheath with the locking mechanism.

3. A needle assembly as claimed in claim 2, wherein a compression spring is disposed intermediate the sheath and the elongate needle mount such that the sheath is biased towards a forward position.

4. A needle assembly adapted to be used with a conventional syringe and including:
   an elongate needle mount having a forward end and a rearward end spaced along an axis, wherein the rearward end of the needle mount is adapted to be mounted to a forward end of a conventional syringe;
   a needle extending axially from the forward end of the elongate needle mount; and
   a sheath mounted on the elongate needle mount for reciprocal axial movement between a forward position whereat the sheath covers the needle and a rearward position whereat the needle is exposed, characterized in that the sheath is in the forward position prior to use of the needle and is movable to the rearward position whereat it is retained during use of the needle, and wherein the rotation of the sheath relative to the elongate needle mount about the axis releases the sheath to return to a final forward position at which the sheath protects the needle to prevent needle sticks, wherein the elongate needle mount has a cross-section along at least a portion of its length to define a first axially extending side and a second axially extending side, said first and second axially extending sides being angularly spaced about said axis, and wherein the sheath includes a resilient member which is adapted to engage said first axially extending side of the elongate needle mount when the needle moves to the rearward position at which the needle is exposed and to engage said second axially extending side of the elongate needle mount when the needle moves to the forward position at which the sheath covers the needle.

5. A needle assembly as claimed in claim 4, wherein the elongate needle mount is substantially square in cross-section along a portion of its length to define first and second pairs of opposed sides, and wherein the sheath includes opposed resilient members which are adapted to engage a pair of the opposed sides of the elongate needle mount.

6. A needle assembly as claimed in claim 5, wherein the sheath is bifurcated at its rearward end to define the opposed resilient members.

7. A needle assembly as claimed in claim 5, wherein initially the resilient members engage a first pair of opposed sides of the elongate needle mount, the rearward end of the first pair of opposed sides terminating in first ramps which retain the opposed resilient members such that the sheath is retained in the rearward position whereat the needle is exposed for use.

8. A needle assembly as claimed in claim 7, wherein the elongate needle mount includes an at least partially circular cross-section portion rearwardly of said first ramps, the at least partially circular cross-section portion being engaged by the opposed resilient members when the sheath is in the rearward position such that the sheath may be axially rotated relative to the needle mount such that after rotation the opposed resilient members align with the second pair of opposed sides of the elongate needle mount.

9. A needle assembly as claimed in claim 8, wherein the forward end of said second pair of opposed sides terminate in second ramps which retain the opposed resilient members such that the sheath is retained in the forward position whereat the needle is protected.

10. A needle assembly as claimed in claim 9, wherein the sheath cannot rotate relative to the needle mount when the sheath is retained in the forward position by virtue of the engagement of the opposed resilient members with outwardly-directed planar surfaces provided on the needle mount forward of the second ramps.

11. A needle assembly as claimed in claim 4, wherein a compression spring is disposed intermediate the sheath and the elongate needle mount such that the sheath is biased to the forward position.

12. A needle mount as claimed in claim 4, wherein the needle extends through the axial length of the elongate needle mount and extends from the rearward end of the elongate needle mount.

* * * * *